United States Patent [19]
Piot et al.

[11] Patent Number: 5,620,693
[45] Date of Patent: Apr. 15, 1997

[54] MASCARA CONTAINING WAX(ES) AND CARBOXYL-FUNCTIONAL FILM-FORMING POLYMER AQUEOUS DISPERSION

[75] Inventors: Bertrand Piot, La Garenne Colombes; Danièle Debert, Savigny Sur Orge; Jeanne Patraud, Paris, all of France

[73] Assignee: L'Oreal, Paris, France

[21] Appl. No.: 341,987

[22] Filed: Nov. 16, 1994

[30] Foreign Application Priority Data

Nov. 24, 1993 [FR] France .................................. 93 14051

[51] Int. Cl.$^6$ .................................................... A61K 7/032
[52] U.S. Cl. ...................... 424/401; 424/70.7; 424/70.11; 424/70.12; 424/70.15; 424/70.16
[58] Field of Search .................................. 424/401, 70.7, 424/70.11, 70.12, 70.15, 70.16

[56] References Cited

U.S. PATENT DOCUMENTS

| | | | |
|---|---|---|---|
| 3,840,338 | 10/1974 | Zviak et al. | 424/70.9 |
| 4,282,203 | 8/1981 | Jacquet et al. | 424/47 |
| 4,445,521 | 5/1984 | Grollier et al. | 424/70.17 |
| 4,871,536 | 10/1989 | Arraudeau et al. | 424/59 |
| 5,053,220 | 10/1991 | Arraudeau et al. | 424/401 |
| 5,194,260 | 3/1993 | Grollier et al. | 424/401 |

FOREIGN PATENT DOCUMENTS

| | | |
|---|---|---|
| 0477053 | 3/1992 | European Pat. Off. . |
| 0530084 | 3/1993 | European Pat. Off. . |
| 0557196 | 8/1993 | European Pat. Off. . |
| 0573229 | 12/1993 | European Pat. Off. . |
| 1477048 | 4/1966 | France . |
| 2091516 | 1/1972 | France . |
| 2328763 | 5/1977 | France . |
| 2439798 | 5/1980 | France . |
| 2528699 | 12/1983 | France . |
| 2573305 | 5/1986 | France . |
| 2680681 | 3/1993 | France . |
| 57-62216 | 4/1982 | Japan . |
| 61-30512 | 2/1986 | Japan . |
| 4-103509 | 4/1992 | Japan . |
| WO91/12793 | 9/1991 | WIPO . |
| WO92/21316 | 10/1992 | WIPO . |

*Primary Examiner*—Robert E. Sellers
*Attorney, Agent, or Firm*—Oliff & Berridge

[57] ABSTRACT

A cosmetic composition comprising in admixture a pseudolatex containing particles of a film-forming polymer having carboxylic acid functional groups, the particles having a mean diameter of between 10 and 300 nm and at least one wax having a melting point of between 60° C. and 110° C. in a proportion of between 2 and 40% by weight with respect to the total weight of the composition. The carboxylic acid functional groups of the polymer are neutralized to a degree of neutralization of between 10 and 80% by a nonvolatile monobasic agent. The pseudolatex is present in a proportion of between 0.8 and 20% by way of solids with respect to the total weight of the composition. The cosmetic composition, used as a mascara, provides enhanced lengthening and beautiful curvature on eyelashes.

13 Claims, No Drawings

MASCARA CONTAINING WAX(ES) AND CARBOXYL-FUNCTIONAL FILM-FORMING POLYMER AQUEOUS DISPERSION

FIELD OF THE INVENTION

The subject of the present invention is a cosmetic composition for making up especially the eyelashes, known as a mascara composition, containing the combination of at least one wax and one pseudolatex.

BACKGROUND

It is common practice to produce mascara compositions containing at least one wax. However, the wax is never used alone because make-up with such compositions proves to be very mediocre, leading to the formation, on the eyelashes, of a nonhomogeneous film which is reflected by the formation of thin films which crack immediately after drying.

In order to find a remedy for them, the joint use of at least one wax and of a film-forming polymer present in solution in the aqueous phase was proposed in French Patents FR 83.09997 (2,528,699) and FR 84.17661 (2,573,305).

Compositions for treating hair and eyelashes containing the combination of a silicone, a latex and an agent for suspending the latex and the silicone and/or a thickening agent have also been proposed in Patent Application PCT WO/92/21316.

Moreover, mascara compositions which do not contain wax have been proposed. Thus, an aqueous mascara composition containing, as film-forming agent, a synthetic latex has been described in Japanese Patent Application Kokai 57-62216.

Although these compositions have made possible a certain improvement in the quality of the make-up products, it has now been surprisingly and unexpectedly observed that, by using the combination of at least one wax and of a specific pseudolatex consisting of particles of a polymer containing partially neutralized carboxylic acid functional groups, mascara compositions were obtained which had excellent cosmetic qualities. In fact, after application, they significantly increase the lengthening and the bending of the eyelashes and, moreover, can be removed with water.

It is recalled that the expression "pseudolatex" is understood to denote a suspension consisting of generally spherical particles of a polymer, these particles being obtained by dispersing the polymer in an appropriate aqueous phase.

SUMMARY OF THE INVENTION

A cosmetic composition of the invention comprises in admixture a pseudo-latex containing particles of a film-forming polymer having carboxylic acid functional groups, the particles having a mean diameter of between 10 and 300 nm and at least one wax having a melting point of between 60° C. and 110° C. in a proportion of between 2 and 40% by weight with respect to the total weight of the composition. The carboxylic acid functional groups of the polymer are neutralized to a degree of neutralization of between 10 and 80% by a non-volatile monobasic agent. The pseudo-latex is present in a proportion of between 0.8 and 20% by weight of solids with respect to the total weight of the composition. The cosmetic composition, used as a mascara, provides enhanced lengthening and beautiful curvature on eyelashes.

DESCRIPTION OF PREFERRED EMBODIMENTS

The expression "pseudolatex" must not be confused with the expression "latex" or "synthetic latex" which is also a suspension consisting of particles of a polymer which are obtained directly by polymerization of one or a number of monomers in an appropriate aqueous phase.

More precisely, the subject of the present invention is a mascara composition containing, as a mixture, a) a pseudolatex consisting of particles of a film-forming polymer containing carboxylic acid functional groups having a mean diameter of between 10 and 300 nm, the said polymer being chosen from:
  (i) vinyl acetate/crotonic acid copolymers,
  (ii) vinyl acetate/crotonic acid/vinyl neodecanoate terpolymers,
  (iii) N-octylacrylamide/methyl methacrylate/hydroxypropyl methacrylate/acrylic acid/tert-butylaminoethyl methacrylate copolymers,
  (iv) methyl vinyl ether/maleic anhydride monoesterified with butanol alternating copolymers,
  (v) acrylic acid/ethyl acrylate/N-tert-butylacrylamide terpolymers, and
  (vi) polymers corresponding to the following general formula:

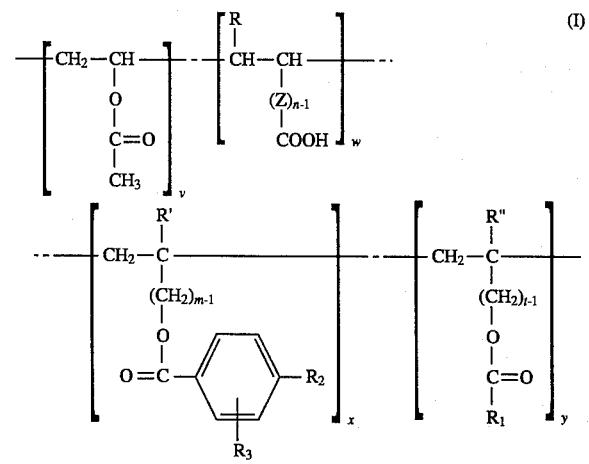

in which:
  R, R' and R", which are identical or different, represent a hydrogen atom or a methyl radical,
  m, n and t are 1 or 2,
  $R_1$ represents a saturated or unsaturated, linear or branched, alkyl radical having from 2 to 21 carbon atoms,
  $R_2$ represents a hydrogen atom or a methyl, ethyl, tert-butyl, ethoxy, butoxy or dodecyloxy radical,
  $R_3$ represents a hydrogen atom, an alkyl radical having from 1 to 4 carbon atoms or an alkoxy radical having from 1 to 4 carbon atoms,
  Z represents a divalent radical taken from the group consisting of:

$-CH_2-$, $-CH_2-O-CH_2-$ and $-CH_2-O-(CH_2)_2-$, v represents from 10 to 91% and preferably from 36 to 84% by weight,
  w represents from 3 to 20% and preferably from 6 to 12% by weight,
  x represents from 4 to 60% and preferably from 6 to 40% by weight, and y represents from 0 to 40% and preferably from 4 to 30% by weight, v+w+x+y being equal to 100%, the carboxylic acid functional groups of the said polymer being neutralized to a degree of neutralization of between 10 and 80% using a nonvolatile monobasic agent, said agent being used alone, and said pseudolatex being present in a proportion of between 0.8 and 20% and preferably between 1 and 10% by weight of solids with respect to the total weight of the composition, and b) at least one wax having a melting point of between 60° C. and 110° C., and preferably between 65° C. and 100° C., in a proportion of between 2 and 40% by weight with respect to the total weight of the composition.

Preferably, the ratio by weight between the neutralized pseudolatex, expressed by weight of solids, and the wax is between 0.025:1 and 2:1 and more particularly Mention may be made, as vinyl acetate/crotonic acid copolymers, of "Luviset CA66" (90/10 vinyl acetate/crotonic acid), with an acid number of 65, of the Company BASF.

Mention may be made, among vinyl acetate/crotonic acid/vinyl neodecanoate terpolymers, of "Resin 28-29-30", with an acid number of 65, of the Company National Starch.

Mention may be made, as N-octylacrylamide/methyl methacrylate/hydroxypropyl methacrylate/acrylic acid/tert-butylaminoethyl methacrylate copolymers, of "Amphomer LV 71", with an acid number of 137, of the Company National Starch.

Mention may be made, among methyl vinyl ether/maleic anhydride monoesterified with butanol alternating copolymers, of "Gantrez ES425" (50/50 methyl vinyl ether/maleic anhydride), with an acid number of 260, of the Company GAF.

Mention may in particular be made, as acrylic acid/ethyl acrylate/N-tert-butylacrylamide terpolymers, of "Ultrahold 8", with an acid number of 62, of the Company BASF.

Mention may be made, as copolymers of formula (I), of those described in French Patent No. 78.30596 (2,439,798) and in particular of the following copolymers:

vinyl acetate/crotonic acid/vinyl 4-tertbutylbenzoate (65/10/25), vinyl acetate/crotonic acid/vinyl 4-tertbutylbenzoate/vinyl neodecanoate (57/10/25/8), vinyl acetate/crotonic acid/vinyl 4-tertbutylbenzoate/vinyl neodecanoate (70/10/10/10), vinyl acetate/crotonic acid/vinyl benzoate/vinyl neodecanoate (70/10/10/10), vinyl acetate/crotonic acid/vinyl 4-tertbutylbenzoate/allyl stearate (70/10/10/10).

The film-forming polymers containing carboxylic acid functional groups such as defined hereinabove are water-insoluble synthetic polymers preferably having a mean molecular weight of between 5,000 and 700,000 measured, for example, by steric exclusion chromatography.

The pseudolatex of the cosmetic compositions according to the invention is obtained according to the known methods for the preparation of pseudolatexes, with the proviso, however, that there are certain specific features which will be mentioned hereinbelow.

The general process for the preparation of the pseudolatexes consists in dissolving a water-insoluble polymer in an organic solvent which is soluble or partially soluble in water, in dispersing, with stirring, the solution thus obtained in water and in then removing the organic solvent by evaporation under vacuum, which leads to a suspension consisting of particles of the polymer whose size is generally less than one μm.

According to this general process, the use of a surface-active agent, a mixture of surface-active agents or a protective colloid polymer or alternatively of a surface-active agent/protective colloid polymer mixture is essential, for the purpose of obtaining good stabilization of the particles.

The film-forming polymers containing carboxylic acid functional groups such as defined hereinabove cannot be used as is in the preparation of the pseudolatexes but must be neutralized to a degree of neutralization of less than 100% for the purpose of preventing them from completely dissolving in the water.

By partial neutralization of the polymers, it was observed that it was possible to obtain particularly stable pseudolatexes in the absence of hydrophilic stabilizing agent or surface-active agent or alternatively of protective colloid.

The degree of neutralization of the film-forming polymers containing carboxylic acid functional groups must therefore be completely neutralized such that they remain insoluble in the water while being soluble in the organic solvent.

It is obvious that the upper limit of the degree of neutralization which it will be advisable not to exceed in order for the polymer to remain insoluble in the water will be a function of the nature of each film-forming polymer containing carboxylic acid functional groups. Generally, this degree of neutralization is generally between 30 and 80%, and preferably between 40 and 70%, if the polymer has less than 2 meq/g of carboxylic acid functional groups, and between 10 and 50%, preferably between 10 and 40%, if the polymer has more than 2 meq/g of carboxylic acid functional groups.

According to the invention, neutralization of the carboxylic acid functional groups is carried out using a nonvolatile monobasic agent chosen, for example, from an inorganic base such as sodium hydroxide or potassium hydroxide or from an aminoalcohol taken from the group consisting of 2-amino-2-methyl-1-propanol (AMP), triethanolamine, triisopropanolamine (TIPA), monoethanolamine, diethanolamine, tri(2-hydroxy-1-propyl)amine, 2-amino-2-methyl-1, 3-propanediol (AMPD) and 2-amino-2-hydroxymethyl-1,3-propanediol.

In the preparation of the pseudolatex used in the compositions according to the invention, neutralization of the carboxylic acid functional groups of the film-forming polymer is carried out in situ in the solution of the polymer in the organic solvent by addition of the specific amount of the nonvolatile monobasic compound. The organic solvent used must be a volatile solvent or a mixture of such solvents having a boiling point below that of water and must be miscible or partially miscible with water.

The organic solvent such as defined hereinabove is preferably chosen from acetone, methyl ethyl ketone, tetrahydrofuran, methyl acetate, ethyl acetate, isopropanol and ethanol.

After obtaining the solution of the partially neutralized polymer in the organic solvent, an emulsion is then prepared by pouring with stirring, into the organic solution obtained, an appropriate amount of water optionally containing an anti-foaming agent whose role will be to facilitate subsequent evaporation of the organic phase.

According to a variant of the process such as defined hereinabove, neutralization of the carboxylic acid functional groups of the polymer in solution in the organic solvent can be carried out during the formation of the emulsion by pouring in an aqueous solution containing the required amount of the non-volatile monobasic compound.

During the formation of the emulsion, stirring is preferably carried out using a shearing disperser of the Moritz or Ultra-Turrax or Raineri type equipped with deflocculating blades.

The emulsion thus obtained is particularly stable without it being necessary to employ a surface-active agent insofar as the carboxylate groups of the polymer are positioned at the interface with the water and protect the droplets from coalescing by electrostatic repulsion.

After formation of the emulsion at a temperature between ambient temperature and approximately 70° C., the organic solvent is then evaporated under reduced pressure until it has been completely removed, evaporation preferably being carried out under gentle heating.

A pseudolatex is thus obtained, that is to say an aqueous dispersion of particles of the film-forming polymer, which is free from any surface-active agent or other hydrophilic stabilizing agent while remaining very stable.

The concentration by weight of the film-forming polymer in the form of particles in the pseudolatex thus obtained is generally between 5 and 50% and preferably between 10 and 25% with respect to the total weight of the pseudolatex.

The mean size of the particles is between 10 and 300 nm but is preferably less than 250 nm.

The polydispersity in size of the particles is relatively low according to this process for the preparation of the pseudolatex; the polydispersity, measured by quasi-elastic light scattering, is generally between 0.1 and 0.40 and preferably less than 0.35.

It is possible to introduce into the pseudo-latexes used in the compositions according to the invention, for the purpose of improving their cosmetic and mechanical properties, a plasticizing agent in a proportion of between 5 and 40% and preferably between 10 and 30% by weight with respect to the weight of the film-forming polymer, the said agent being distributed according to its partition coefficient between the particles and the aqueous phase of the pseudolatex.

The plasticizing agent, which can be of the hydrophilic or hydrophobic type, is preferably introduced by mixing in the organic solvent during the preparation of the pseudolatex and especially when it is of the hydrophobic type.

When the plasticizing agent is of the hydrophilic type, it can be introduced into the aqueous phase after formation of the pseudolatex.

Mention may be made, among plasticizing agents which can be used in the compositions according to the invention, of:

"Carbitols" of the Company Union Carbide, namely "Carbitol" or diethylene glycol ethyl ether, "methyl Carbitol" or diethylene glycol methyl ether, "butyl Carbitol" of diethylene glycol butyl ether or alternatively "hexyl Carbitol" or diethylene glycol hexyl ether, "Cellosolves" of the Company Union Carbide, namely "Cellosolve" or ethylene glycol ethyl ether, "butyl Cellosolve" or ethylene glycol butyl ether, or "hexyl Cellosolve" or ethylene glycol hexyl ether, propylene glycol derivatives and in particular propylene glycol phenyl ether, propylene glycol diacetate, dipropylene glycol butyl ether, tripropylene glycol butyl ether and "Dowanols" of the Company Dow Chemical, namely "Dowanol PM" or propylene glycol methyl ether, "Dowanol DPM" or dipropylene glycol methyl ether and "Dowanol TPM" or tripropylene glycol methyl ether.

Mention may alternatively be made of:

diethylene glycol methyl ether or "Dowanol DM" of the Company Dow Chemical, castor oil oxyethylenated with 40 mol of ethylene oxide such as that sold by the Company Rhône-Poulenc under the name of "Mulgofen EL-719", benzyl alcohol, triethyl citrate sold by the Company Pfizer under the name of "Citroflex-2", 1,3-butylene glycol, diethyl, dibutyl and diisopropyl phthalates and adipates, diethyl and dibutyl tartrates, diethyl, dibutyl and di(2-ethylhexyl) phosphates, and glyceryl esters such as glyceryl diacetate (diacetin) and glyceryl triacetate (triacetin).

Use is preferably made of a plasticizing agent chosen from the group consisting of dipropylene glycol methyl ether, tripropylene glycol methyl ether, diethyl adipate and diisopropyl adipate.

The waxes used in the mascara compositions according to the invention are chosen from solid and rigid waxes of animal, plant, inorganic or synthetic origin and their mixtures.

The hardness of these waxes, measured by the method of penetration of a needle, is generally between 3 and 40.

This method, described in the NFT 004 and ASTMD5 standards, the French and American standards respectively, consists in measuring, at a temperature of 25° C., the depth of penetration, expressed in tenths of a millimeter, of a standardized needle (weighing 2.5 g and placed in a needle holder weighing 47.5 g, i.e. 50 g in total) placed on the wax for 5 seconds.

Mention may be made, among animal waxes, of beeswax, lanolin wax and Chinese insect waxes.

Mention may especially be made, among plant waxes, of rice wax, carnauba wax, candelilla wax, ouricury wax, cork fibre wax, sugar cane wax, Japan wax and sumach wax.

Mention may especially be made, among inorganic waxes, of montan wax, microcrystalline waxes, paraffins and ozocerite.

Mention may especially be made, among synthetic waxes, of polyethylene waxes, waxes obtained by the Fischer-Tropsch synthesis and waxy copolymers and their esters.

It is also possible to use, in the compositions according to the invention, waxes obtained by catalytic hydrogenation of animal or vegetable oils having linear or branched $C_8$–$C_{32}$ fatty chains.

Among the latter, mention may especially be made of hydrogenated jojoba oil, hydrogenated sunflower oil, hydrogenated castor oil, hydrogenated coconut oil and hydrogenated lanolin oil.

The mascara compositions according to the invention can additionally contain pigments.

These pigments can be organic or inorganic or can also be iridescent pigments. Such pigments are well known and are in particular described in Patent FR 83.09997 (2,528,699).

The proportion of pigments in the mascara compositions according to the invention is generally between 3 and 25% by weight with respect to the total weight of the composition, depending on the coloring and intensity of coloring desired.

The mascara compositions according to the invention can be provided in various forms. They can, in particular, be provided in the form of oil-in-water or water-in-oil emulsions or in the form of dispersions.

According to a preferred embodiment of the mascara compositions according to the invention, the latter are provided in the form of emulsions containing at least one anionic or nonionic surface-active agent in an amount of between 2 and 30% by weight with respect to the total weight of the composition.

Mention may especially be made, among anionic surface-active agents which can be used alone or as a mixture, of the alkali metal salts, the ammonium salts, the amine salts or the aminoalcohol salts of the following compounds:

- alkyl sulfates, alkyl ether sulfates, alkylamide sulfates, ether sulfates, alkylaryl polyether sulfates or monoglyceride sulfates,
- alkyl sulfonates, alkylamide sulfonates, alkylaryl sulfonates, α-olefin sulfonates or paraffin sulfonates,
- alkyl sulfosuccinates, alkyl ether sulfosuccinates or alkylamide sulfosuccinates,
- alkyl sulfosuccinamates,
- alkyl sulfoacetates or alkyl polyglycerol carboxylates,
- alkyl phosphates or alkyl ether phosphates,
- N-acyl sarcosinates, N-acyl polypeptidates, acyl isethionates and N-acyl taurates.

The terms alkyl and acyl used hereinabove mean a chain generally having from 12 to 18 carbon atoms.

Mention may also be made, as anionic surface-active agents which can be used in the compositions according to the invention, of salts of fatty acids such as those of oleic, ricinoleic, palmitic or stearic acid or the acids of coconut oil or of hydrogenated coconut oil, and in particular amine salts such as amine stearates.

Mention may also be made, as anionic surface-active agents, of acyl lactylates in which the acyl radical comprises from 8 to 20 carbon atoms and carboxylic acids of polyglycolic ethers corresponding to the formula:

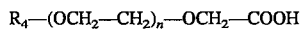

R$_4$—(OCH$_2$—CH$_2$)$_n$—OCH$_2$—COOH in which:

R$_4$ represents a linear alkyl radical having from 12 to 18 carbon atoms and n is an integer between 5 and 15, and the salts of the said acids. Use is preferably made, as anionic surface-active agent, of amine stearates.

Mention may especially be made, among nonionic surface-active agents which can be used alone or as a mixture in the mascara compositions according to the invention, of polyethoxylated, polypropoxylated or polyglycerolated fatty acids, alkylphenols and alcohols with fatty chain having from 8 to 18 carbon atoms.

Mention may also be made of copolymers of ethylene and propylene oxides, condensates of ethylene and propylene oxides with fatty alcohols, polyethoxylated fatty amides, polyethoxylated fatty amines, ethanolamines, fatty acid esters of glycol, optionally oxyethylenated fatty acid esters of sorbitan, fatty acid esters of sucrose, fatty acid esters of polyethylene glycols, phosphoric triesters and fatty acid esters of glucose derivatives.

Mention may also be made of condensation products of a monoalcohol, an alpha-diol, an alkylphenol, an amide or a diglycolamide with glycidol or a precursor of glycidol such as described in French Patent FR 71.17206 (2,091,516), of formula:

R$_5$—CHOH—CH$_2$—O—(CH$_2$—CHOH—CH$_2$—O)$_p$—H in which:

R$_5$ represents an aliphatic, cycloaliphatic or arylaliphatic radical preferably having between 7 and 21 carbon atoms, it being possible for the aliphatic chains to contain ether, sulfide or hydroxymethylene groups, and p is an integer between 1 and 10.

Mention may additionally be made of compounds described in Patent FR 1,477,048 of formula:

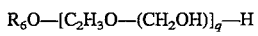

R$_6$O—[C$_2$H$_3$O—(CH$_2$OH)]$_q$—H in which:

R$_6$ represents an alkyl, alkenyl or alkylaryl radical and q is a statistical value between 1 and 10.

Mention may further be made of compounds described in French Patent FR 76.31975 (2,328,763) of formula:

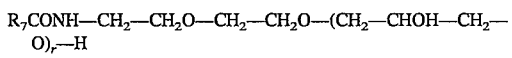

R$_7$CONH—CH$_2$—CH$_2$O—CH$_2$—CH$_2$O—(CH$_2$—CHOH—CH$_2$—O)$_r$—H in which:

R$_7$ represents a saturated or unsaturated, linear or branched, aliphatic radical of natural or synthetic origin which can optionally contain one or a number of hydroxyl group(s) and which has between 8 and 30 carbon atoms and r is an integer or decimal number between 1 and 5 and denotes the mean degree of condensation.

Use is preferably made, as nonionic surface-active agent of a mixture of oil(s) and/or of fatty alcohol or else of polyethoxylated or polyglycerolated alcohols such as polyethoxylated cetylstearyl or stearyl alcohols.

The mascara compositions according to the invention can additionally comprise at least one conventional additive chosen from an emollient, a preserving agent, a sequestering agent, a fragrance, a thickening agent, an oil, a silicone, a cohesion agent, a basifying or acidifying agent, a water-soluble polymer and a filler.

The thickening agents which can be used in the mascara compositions according to the invention can be of natural or synthetic origin.

Mention may especially be made, among thickening agents of natural origin, of various types of gums such as gum arabic, guar gum or carob gum.

Mention may especially be made, among thickening agents of synthetic origin, of cellulose derivatives such as hydroxyethyl cellulose and carboxymethyl cellulose, starch derivatives, cellulose ether derivatives possessing quaternary ammonium groups, cationic polysaccharides, salts of acrylic or methacrylic polymers, polyenes and polysiloxanes.

It is also possible to obtain a thickening of the mascara compositions according to the invention by addition of a mixture of polyethylene glycol and polyethylene glycol distearate and/or stearate or of a mixture of phosphoric esters and fatty amides.

Mention may especially be made, among watersoluble polymers which can be used in the mascara compositions according to the invention, of protein derivatives of animal or plant origin and more particularly keratin derivatives such as keratin hydrolyzates and sulfonic keratins, polyvinylpyrrolidone, vinyl copolymers such as the copolymer of methyl vinyl ether and maleic anhydride or the copolymer of vinyl acetate and crotonic acid, glycoaminoglycans, hyaluronic acid and its derivatives and deoxyribonucleic acid and its salts.

Mention may especially be made, among the fillers which can be used in the mascara compositions according to the invention, of those described in Patent Application FR 91.10791 (2,680,681).

A number of examples of the preparation of the pseudolatexes, and examples of mascara according to the invention, will now be given by way of illustration.

PSEUDOLATEX PREPARATION EXAMPLES

EXAMPLE I

Preparation of the pseudolatex of the vinyl acetate/crotonic acid/vinyl 4-tert-butylbenzoate (65/10/25) copolymer neutralized to 50% from its acid number The preparation of this copolymer is described in Example 19 of French Patent No. 78.30596 (2,439,798) and is provided in the form of beads having a diameter of 0.5 to 1 mm.

40 g of the copolymer defined hereinabove (acid number: 65) are added little by little with stirring to a homogeneous solution of 110 g of acetone, 2.07 g of 2-amino-2-methyl-1-propanol (amount corresponding to 50% of neutralization from the acid number) and 8 g of monomethyl ether of tripropylene glycol.

After stirring at room temperature for 30 minutes, the polymer has completely dissolved.

An aqueous phase is added over approximately 5 minutes, with stirring using a shearing disperser of the Ultra-Turrax type at 2000 rev/min, to the organic phase thus obtained in order to produce the emulsion, the aqueous phase consisting of 109.54 g of deionized water and 0.456 g of a silicone anti-foaming agent "Burst RSD 10".

After the end of the addition of the aqueous phase, stirring is continued for 10 to 15 min at room temperature, which makes it possible to lead to a translucent and stable emulsion being obtained.

Concentration is then carried out using a rotary evaporator under partial vacuum at a temperature below 45° C. After completely removing the acetone, a stable, milky and only slightly viscous dispersion is obtained.

The size of the particles was measured by quasi-elastic light scattering with a Coulter model M4 and gave the following results:

Mean size of the particles: 67 nm

Polydispersity factor: 0.22.

EXAMPLE II

Preparation of the pseudolatex of the N-octylacrylamide/methyl methacrylate/hydroxypropyl methacrylate/acrylic acid/tert-butylaminoethyl methacrylate copolymer ("Amphomer LV 71" of the Company National Starch) neutralized to 30% from its acid number A pseudolatex is prepared at room temperature, according to a procedure analogous to that described previously, from 150 g of the "Amphomer LV 71" copolymer added to a homogeneous solution of 1063 g of tetrahydrofuran, 9.80 g of 2-amino-2-methyl-1-propanol (amount corresponding to 30% of neutralization from the acid number of the "Amphomer LV 71" copolymer) and 30 g of monomethyl ether of tripropylene glycol, and from an aqueous phase consisting of 812 g of deionized water and 1.71 g of a silicone anti-foaming agent "Burst RSD 10".

A pseudolatex is thus obtained whose polymer concentration is 15% by weight with respect to the total weight of the composition.

The size of the particles was measured by quasielastic light scattering with a Coulter model M4 and gave the following results:

Mean size of the particles: 299 nm

Polydispersity factor: 0.33.

EXAMPLE III

Preparation of the pseudolatex of the 90/10 vinyl acetate/crotonic acid copolymer ("Luviset CA 66" of the Company B.A.S.F.) neutralized to 50% from its acid number 60 g of the "Luviset CA 66" copolymer in the powder form (acid number: 65) are added little by little with stirring to a homogeneous solution of 22.5 g of methyl ethyl ketone, 3.5 g of 2-amino-2-methyl-1-propanol (AMP) (amount corresponding to 50% of neutralization from the acid number of "Luviset CA 66" copolymer) and 12 g of monomethyl ether of tripropylene glycol.

After continuing to stir for 30 minutes, the copolymer has completely dissolved.

An aqueous phase is added, with stirring using a Moritz disperser at 2500 rev/min, to the organic phase thus obtained in order to produce the emulsion, the aqueous phase consisting of 325 g of deionized water and 0.69 g of a silicone anti-foaming agent "Burst RSD 10".

Addition of the aqueous phase is carried out over approximately 15 minutes and stirring is then maintained at 3000 rev/min for 15 minutes. A moderately viscous emulsion of milky appearance is thus obtained.

All the organic solvent is then evaporated using a rotary evaporator under partial vacuum and heating at approximately 40–45° C. Evaporation is continued until all the methyl ethyl ketone has been removed, by respecting the azeotrope with water.

The amount of water removed by formation of the azeotrope is then readded to the dispersion to obtain a pseudolatex having a concentration of film-forming polymer of 15%. The pseudolatex obtained is stable and moderately viscous and has an opaque, slightly bluish appearance.

The size of the particles was measured by quasielastic light scattering with a Coulter model M4 and gave the following results:

Mean size of the particles: 247 nm

Polydispersity factor: 0.47.

MASCARA EXAMPLES

EXAMPLE 1

Mascara cream

| PART A | |
|---|---|
| Triethanolamine stearate | 12.0 g |
| Beeswax | 6.0 g |
| Carnauba wax | 1.0 g |
| Paraffin | 3.5 g |
| PART B | |
| Black iron oxides | 6.0 g |
| PART C | |
| Hydroxyethyl cellulose marketed under the name of "Cellosize QP" by the Company Amerchol | 1.0 g |
| Gum arabic | 2.0 g |
| Keratin hydrolyzate | 1.8 g |
| PART D | |
| Pseudolatex of Example I | 5.0 g |
| Preserving agents q.s. | |
| Water q.s. for | 100 g |

This mascara is obtained by bringing the ingredients of Part A to 85° C., at which Part B is added and stirring is carried out using a turbine.

The water of the preparation is then boiled, the preserving agents are added and then, at 85° C., the ingredients of Part C are added.

The aqueous phase obtained is then added (85° C.) to Part A (80° C.) with stirring using a turbine (emulsification at 30° C.) and then the pseudolatex of Part D is finally added and stirring is carried out using a paddle.

EXAMPLE 2

Mascara

A mascara having the following composition is prepared according to the same procedure as in Example 1:

| PART A | |
|---|---|
| Triethanolamine stearate | 8.0 g |
| Glyceryl stearate marketed under the name of "Geleol" by the Company Gattefosse | 3.0 g |
| Beeswax | 8.0 g |
| Carnauba wax | 2.0 g |
| Paraffin | 5.0 g |
| PART B | |
| Black iron oxides | 5.0 g |
| PART C | |
| Hydroxyethyl cellulose marketed under the name of "Cellosize QP" by the Company Amerchol | 1.2 g |
| Gum arabic | 2.0 g |
| PART D | |
| Pseudolatex of Example III | 7.0 g |
| Preserving agents q.s. | |
| Water q.s. for | 100 g |

EXAMPLE 3

Mascara

A mascara having the following composition is prepared according to the same procedure as in Example 1:

| PART A | |
|---|---|
| Triethanolamine stearate | 12.0 g |
| Beeswax | 5.0 g |
| Carnauba wax | 1.5 g |
| Paraffin | 4.0 g |
| PART B | |
| Carbon black | 3.0 g |
| PART C | |
| Hydroxyethyl cellulose marketed under the name of "Cellosize QP" by the Company Amerchol | 0.8 g |
| Gum arabic | 2.0 g |
| Keratin hydrolyzate marketed under the name of "Kerasol" by the Company Croda | 2.0 g |
| PART D | |
| Pseudolatex of Example II | 13.3 g |
| Preserving agents q.s. | |
| Water q.s. for | 100 g |

The cosmetic effect of this mascara obtained by replacing, in the same composition, the pseudolatex of Example II with the same amount of a 15% solution of the film-forming polymer "Amphomer LV 71", neutralized to 100% from its acid number with 2-amino-2-methyl-1propanol, was compared. When the mascara according to the invention is used, the eyelashes after make-up are markedly longer and have a more pronounced curvature than the eyelashes treated using the comparison mascara.

We claim:

1. A mascara composition comprising in admixture:
a) an aqueous dispersion of particles of a film-forming polymer having carboxylic acid functional groups, said particles having a mean diameter of between 10 and 300 nm, and said polymer being selected from the group consisting of:
   (i) vinyl acetate/crotonic acid copolymers,
   (ii) vinyl acetate/crotonic acid/vinyl neodecanoate terpolymers,
   (iii) N-octylacrylamide/methyl methacrylate/hydroxypropyl methacrylate/acrylic acid/tertbutylaminoethyl methacrylate copolymers,
   (iv) methyl vinyl ether/maleic anhydride mono-esterified with butanol alternating copolymers,
   (v) acrylic acid/ethyl acrylate/N-tertbutyl-acrylamide terpolymers, and
   (vi) polymers corresponding to the following general formula:

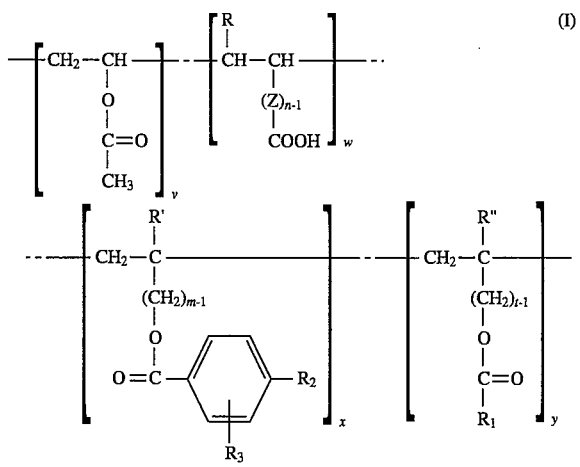

in which:
R, R' and R", which are identical or different, represent a hydrogen atom or a methyl radical;
m, n and t are 1 or 2;
$R_1$ represents a saturated or unsaturated, linear or branched, alkyl radical having from 2 to 21 carbon atoms;
$R_2$ represents a hydrogen atom or a methyl, ethyl, tertbutyl, ethoxy, butoxy or dodecyloxy radical;
$R_3$ represents a hydrogen atom, an alkyl radical containing 1 to 4 carbon atoms or an alkoxy radical having from 1 to 4 carbon atoms; and
Z represents a divalent radical selected from the group consisting of:

—$CH_2$—, —$CH_2$—O—$CH_2$— and —$CH_2$—O—$(CH_2)_2$—;

v represents from 10 to 91% by weight,
w represents from 3 to 20% by weight,
x represents from 4 to 60% by weight, and
y represents from 0 to 40% by weight,
v+w+x+y being equal to 100%;
the carboxylic acid functional groups of said polymer being neutralized to a degree of neutralization of between 10 and 80% by a nonvolatile monobasic agent, said agent being used alone; and
said aqueous dispersion of particles being present in a proportion of between 0.8 and 20% by weight of solids with respect to the total weight of the composition; and b) at least one wax having a melting point of between 60° C. to 110° C., in a proportion of between 2 and 40% by weight with respect to the total weight of the composition.

2. The mascara composition of claim 1, wherein the ratio by weight between the neutralized dispersion, expressed by weight of solids, and the wax is between 0.025:1 and 2:1.

3. The mascara composition of claim 1, wherein the film-forming polymer having carboxylic acid functional groups has a mean molecular weight of between 5,000 and 700,000.

4. The mascara composition of claim 1, wherein the film-forming polymer containing carboxylic acid functional groups is neutralized using a non-volatile agent selected from the group consisting of sodium hydroxide, potassium hydroxide, 2-amino-2-methyl-1-propanol, triethanolamine, triisopropanolamine, monoethanolamine, diethanolamine, tri(2-hydroxy-1-propyl)amine, 2-amino-2-methyl-1,3-propanediol and 2-amino-2-hydroxy-methyl-1,3-propanediol.

5. The mascara composition of claim 1, wherein if said film-forming polymer has less than 2 meq/g of carboxylic acid functional groups, the degree of neutralization is between 30 and 80%.

6. The mascara composition of claim 1, wherein if said film-forming polymer has more than 2 meq/g of carboxylic acid functional groups, the degree of neutralization is between 10 and 50%.

7. The mascara composition of claim 1, wherein the aqueous dispersion of particles contains a plasticizing agent in a proportion of between 5 and 40% by weight with respect to the weight of the film-forming polymer, said plasticizing agent being distributed according to its partition coefficient between the particles and the aqueous phase of the dispersion.

8. The mascara composition of claim 1, wherein said wax is selected from the group consisting of beeswax, lanolin wax, Chinese insect wax, rice wax, carnauba wax, candelilla wax, ouricury wax, cork fiber wax, sugar cane wax, Japan wax, sumach wax, montan wax, microcrystalline waxes, paraffins, ozocerite, polyethylene waxes and hydrogenated oils.

9. The mascara composition of claim 1, which further contains pigments in a proportion of between 3 and 25% by weight with respect to the total weight of the composition.

10. The mascara composition of claim 1, wherein said composition is in the form of an oil-in-water or water-in-oil emulsion or of a dispersion.

11. The mascara composition of claim 10, wherein said composition is in the form of an emulsion containing at least one anionic or nonionic surface-active agent in a proportion of between 2 and 30% by weight with respect to the total weight of the composition.

12. The mascara composition of claim 1, which further contains a cosmetic additive selected from the group consisting of an emollient, a preserving agent, a sequestering agent, a fragrance, a thickening agent, an oil, a silicone, a cohesion agent, a basifying or acidifying agent, a water-soluble polymer and a filler.

13. A mascara composition according to claim 1, wherein said particles possess a polydispersity in size between 0.1 and 0.40.

* * * * *